(12) United States Patent
Laufer et al.

(10) Patent No.: US 9,512,299 B2
(45) Date of Patent: Dec. 6, 2016

(54) CARBODIIMIDES HAVING TERMINAL UREA AND/OR URETHANE GROUPS, METHODS FOR PRODUCING SAID CARBODIIMIDES, AND USE OF SAID CARBODIIMIDES

(71) Applicant: Rhein Chemie Rheinau GmbH, Mannheim (DE)

(72) Inventors: Wilhelm Laufer, Ellerstadt (DE); Benjamin Bechem, Mannheim (DE); Armin Eckert, Oberhausen-Rheinhausen (DE)

(73) Assignee: Rhein Chemie Rheinau GmbH, Mannheim (DE)

( * ) Notice: Subject to any disclaimer, the term of this patent is extended or adjusted under 35 U.S.C. 154(b) by 0 days.

(21) Appl. No.: 14/890,971

(22) PCT Filed: May 9, 2014

(86) PCT No.: PCT/EP2014/059578
§ 371 (c)(1),
(2) Date: Nov. 13, 2015

(87) PCT Pub. No.: WO2014/184116
PCT Pub. Date: Nov. 20, 2014

(65) Prior Publication Data
US 2016/0096951 A1    Apr. 7, 2016

(30) Foreign Application Priority Data
May 13, 2013  (EP) .................................... 13167511

(51) Int. Cl.
| | |
|---|---|
| C08K 5/29 | (2006.01) |
| C07C 271/28 | (2006.01) |
| C07C 275/40 | (2006.01) |
| C08G 18/02 | (2006.01) |
| C07C 273/18 | (2006.01) |
| C07C 267/00 | (2006.01) |

(52) U.S. Cl.
CPC ............. C08K 5/29 (2013.01); C07C 267/00 (2013.01); C07C 271/28 (2013.01); C07C 273/1818 (2013.01); C07C 275/40 (2013.01); C08G 18/025 (2013.01)

(58) Field of Classification Search
CPC ....... C08K 5/29; C07C 271/28; C07C 275/40; C07C 273/1818; C07C 267/00; C08G 18/025
See application file for complete search history.

(56) References Cited

U.S. PATENT DOCUMENTS

| | | | | |
|---|---|---|---|---|
| 2,941,983 A | * | 6/1960 | Smeltz .................. | C08G 18/025 521/901 |
| 4,076,945 A | * | 2/1978 | Elmer .................... | C08G 18/00 528/44 |
| 5,498,747 A | | 3/1996 | Pohl et al. | |

FOREIGN PATENT DOCUMENTS

| | | |
|---|---|---|
| DE | 1130594 B | 5/1962 |
| DE | 102004041605 A1 | 3/2006 |

OTHER PUBLICATIONS

Brown, Daniel W., et al., "Kinetics of the Reaction between Polyester Acid and Carbodiimide in Dry Polyester Diols and in a Polyester Polyurethane", Macromolecules 1981, 14, American Chemical Society, Washington DC. USA, pp. 559-663.

Campbell, T.W., et al., "Carbodiimides, IV, High Polymers Containing the Carbodiimide Repeat Unit", Journal of Organic Chemistry, American Chemical Society, vol. 28, Aug. 1963, Washington, DC, USA, pp. 2069-2075.

European Search Report from European Application No. 13167511, dated Sep. 20, 2013, two pages.

* cited by examiner

*Primary Examiner* — John Uselding

(57) ABSTRACT

The invention relates to novel carbodiimides having terminal urea and/or urethane groups, methods for the preparation thereof and use thereof as stabilizers in ester-based polyols, in polyethylene terephthalate (PET), in polybutylene terephthalate (PET), in polytrimethylene terephthalate (PTT), in copolyesters, in thermoplastic polyester elastomers (TPE E), in ethylene vinyl acetate (EVA), in polylactic acid (PLA) and/or in PLA derivatives, in polybutylene adipate terephthalates (PBAT), in polybutylene succinates (PBS), in polyhydroxyalkanoates (PHA), in blends, in triglycerides, in thermoplastic polyurethanes, in polyurethane elastomers, in PU adhesives, in PU casting resins, for PU coatings or in PU foams.

21 Claims, No Drawings

CARBODIIMIDES HAVING TERMINAL UREA AND/OR URETHANE GROUPS, METHODS FOR PRODUCING SAID CARBODIIMIDES, AND USE OF SAID CARBODIIMIDES

The invention relates to novel carbodiimides having terminal urea and/or urethane groups, methods for the preparation thereof and use thereof as stabilizers in ester-based polyols, in polyethylene terephthalate (PET), in polybutylene terephthalate (PBT), in polytrimethylene terephthalate (PTT), in copolyesters, in thermoplastic polyester elastomers (TPE E), in ethylene vinyl acetate (EVA), in polylactic acid (PLA) and/or in PLA derivatives, in polybutylene adipate terephthalates (PBAT), in polybutylene succinates (PBS), in polyhydroxyalkanoates (PHA), in blends, in triglycerides, in thermoplastic polyurethanes, in polyurethane elastomers, in PU adhesives, in PU casting resins, for PU coatings or in PU foams.

Carbodiimides have been found to be useful in many applications, for example as hydrolysis stabilizers for thermoplastics, polyols, polyurethanes, triglycerides and lubricating oils etc.

Preference is given to using sterically hindered aromatic monocarbodiimides for this purpose. 2,6-Diisopropylphenylcarbodiimide is especially known in this context. These monocarbodiimides, however, have the disadvantage of being volatile even at low temperatures. They are thermally unstable and may eliminate toxic, volatile substances. Other carbodiimides, as described in EP 0 628 541 A1, are based on specific raw materials which are very expensive to purchase. These also have high viscosities at room temperature making these carbodiimides difficult to handle. Furthermore, in certain PU, PET, PLA or lubricant applications, their reactivity and/or their stabilizing effect is insufficient at the standard concentrations used. Polymeric carbodiimides based on cheap raw materials, such as those described in DE-A 2248751 and U.S. Pat. No. 2,941,983, are not sufficiently sterically hindered and do not show a good hydrolysis-stabilizing effect in the majority of ester-based polymers. Highly sterically hindered carbodiimides, such as those based on triisopropylphenyl isocyanate, are very effective but have very high melting points, are insoluble and cannot be introduced into the starting materials of the polyurethane or only with considerable expenditure in terms of equipment and time.

Therefore, there exists a need for novel carbodiimides not having the disadvantages of the prior art, which possess high thermal stability and may be used for protection against hydrolysis of ester-based polymers.

This object was achieved, surprisingly, by the use of particular aromatic carbodiimides.

The object of the present invention, therefore, are carbodiimides having terminal urea and or urethane groups of the Formula (I)

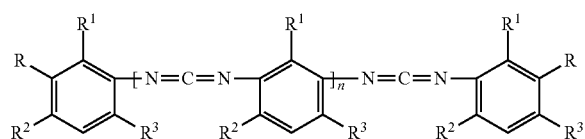

in which
R may be the same or different and is selected from the group of —NHCONHR$^{I}$, —NHCONR$^{I}$R$^{II}$ and —NHCOOR$^{III}$ residues, where R$^{I}$ and R$^{II}$ are the same or different and are a $C_1$-$C_{22}$-alkyl, $C_6$-$C_{12}$-cycloalkyl, $C_6$-$C_{18}$-aryl or $C_6$-$C_{18}$-aralkyl residue and R$^{III}$ is equal to $C_1$-$C_{22}$-alkyl, preferably $C_1$-$C_6$-alkyl, particularly preferably methyl, ethyl or i-propyl, $C_6$-$C_{12}$-cycloalkyl, preferably $C_6$-cycloalkyl, $C_6$-$C_{18}$-aryl or $C_6$-$C_{18}$-aralkyl, and also an unsaturated alkyl residue (e.g. an oleyl residue) having 2-22, preferably 12-20, particularly preferably 16-18 carbon atoms, or an alkoxypolyoxyalkylene residue, R$^1$, R$^2$ and R$^3$ are each independently methyl or ethyl, wherein each benzene ring has only one methyl group and n=0 to 20, preferably n=1 to 10.

The carbodiimide content (NCN content, measured by titration with oxalic acid) of the carbodiimides according to the invention is preferably 2-14% by weight.

Preference is given to carbodiimides of the formula (I) where R=—NHCOOR$^{III}$, where R$^{III}$ is an alkoxypolyoxyalkylene residue, R$^1$, R$^2$ and R$^3$ are each independently methyl or ethyl, wherein each benzene ring has only one methyl group and n=0 to 20, preferably n=1 to 10, particularly preferably n=1 to 4, especially preferably n=2 to 3. The carbodiimide content of these preferred carbodiimides is preferably 2-10% by weight, particularly preferably 4-8% by weight, especially preferably 5-7% by weight.

Preferred alkoxypolyoxyalkylene residues are polyethylene glycol monomethyl ethers with molar masses of 200-600 g/mol, particularly preferably 350-550 g/mol.

Preference is likewise given to carbodiimides of the formula (I) where R=—NHCOOR$^{III}$, where R$^{III}$ is equal to $C_1$-$C_{22}$-alkyl, preferably $C_1$-$C_6$-alkyl, particularly preferably methyl, ethyl or i-propyl, $C_6$-$C_{12}$-cycloalkyl, preferably $C_6$-cycloalkyl, and R$^1$, R$^2$ and R$^3$ are each independently methyl or ethyl, wherein each benzene ring has only one methyl group and n=0 to 20, preferably n=1 to 10, particularly preferably n=3 to 8. The carbodiimide content of these preferred carbodiimides is preferably 4-13% by weight, particularly preferably 10-13% by weight.

These preferred carbodiimides of the formula (I) where R=—NHCOOR$^{III}$, where R$^{III}$ is equal to $C_1$-$C_{22}$-alkyl, preferably $C_1$-$C_6$-alkyl, particularly preferably methyl, ethyl or i-propyl, $C_6$-$C_{12}$-cycloalkyl, preferably $C_6$-cycloalkyl and R$^1$, R$^2$ and R$^3$ are each independently methyl or ethyl, wherein each benzene ring has only one methyl group and n=0 to 20, preferably n=1 to 10, particularly preferably n=3 to 8, are solid and have softening points >40° C. and are therefore outstandingly suitable for stabilizing ester-based polymers, which are preferably selected from the group of polyethylene terephthalate (PET), polybutylene terephthalate (PBT), polytrimethylene terephthalate (PTT), thermoplastic polyurethanes (TPU), copolyesters such as the modified polyester of cyclohexanediol and terephthalic acid (PCTA), thermoplastic polyester elastomers (TPE E), ethylene vinyl acetate (EVA), polylactic acid (PLA) and/or PLA derivatives, polyhydroxyalkanoates (PHA), polybutylene adipate terephthalate (PBAT), polybutylene succinate (PBS), or are suitable in blends such as PA/PET or PHA/PLA blends which the present invention also relates to.

In the method according to the invention for stabilizing the ester-based polymers, the carbodiimides of the formula (I) where R=—NHCOOR$^{III}$, where R$^{III}$ is equal to $C_1$-$C_{22}$-alkyl, preferably $C_1$-$C_6$-alkyl, particularly preferably methyl, ethyl or i-propyl, $C_6$-$C_{12}$-cycloalkyl, preferably $C_6$-cycloalkyl and R$^1$, R$^2$ and R$^3$ are each independently methyl or ethyl, wherein each benzene ring has only one methyl group and n=0 to 20, preferably n=1 to 10, particularly preferably n=3 to 8, are added by means of solids metering units to the ester-based polymers selected from the group comprising polyethylene terephthalate (PET), polybutylene terephthalate (PBT), polytrimethylene terephthalate (PTT), thermoplastic polyurethanes (TPU), copolyesters such as the modified polyester of cyclohexanediol and terephthalic acid (PCTA), thermoplastic polyester elastomers (TPE E), ethylene vinyl acetate (EVA), polybutylene adipate terephthalate (PBAT), polybutylene succinate (PBS), polylactic acid (PLA) and/or PLA derivatives, polyhydroxyalkanoates (PHA), or in blends such as PA/PET or PHA/PLA blends.

Solids metering units in the context of the invention are preferably: single, double or multi-shaft extruders, continuously operating co-kneaders (Buss type) and kneaders operating in batch mode, e.g. Banbury type and other conventional units in the polymer industry.

The concentration of the carbodiimides of the formula (I) according to the invention in the ester-based polymers is preferably 0.1-5% by weight, preferably 0.5-3% by weight, particularly preferably 1-2% by weight.

In a further embodiment of the invention, carbodiimides of the formula (I) are preferably those in which R is equal to —NHCOOR$^{III}$, where R$^{III}$ is a saturated and/or unsaturated alkyl residue having 2-22, preferably 12-20, particularly preferably 16-18 carbon atoms, and R$^1$, R$^2$ and R$^3$ are each independently methyl or ethyl, wherein each benzene ring has only one methyl group and n=0 to 20, preferably n=1 to 10, particularly preferably n=1 to 4, especially preferably n=2 to 3. The carbodiimide content of these preferred carbodiimides is preferably 2-10% by weight, particularly preferably 4-8% by weight, especially preferably 5-7% by weight.

The carbodiimides according to the invention also preferably have average molar masses (Mw) of 1000-5000 g/mol, preferably 1500-4000 g/mol, particularly preferably 2000-3000 g/mol.

Furthermore, preference is given to carbodiimides having a polydispersity D=Mw/Mn of 1.2-2, particularly preferably 1.4-1.8.

The scope of the invention includes all general residue definitions, indices, parameters and illustrations mentioned above and below, and those mentioned in preferred ranges with one another, i.e. also any combinations between the respective ranges and preferred ranges.

The present invention also relates to the preparation of the carbodiimides according to the invention by carbodiimidization of aromatic diisocyanates of the formula (II)

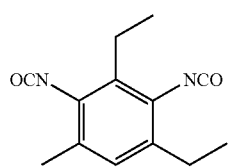

(II)

and/or of the formula (III)

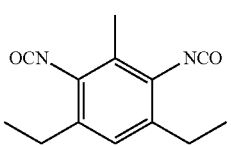

(III)

with elimination of carbon dioxide at temperatures of 80° C. to 200° C. in the presence of catalysts and optionally solvent and the subsequent terminal functionalization of the free NCO groups with primary or secondary amines or alcohols and/or alkoxypolyoxyalkylene alcohols.

Preference is given to using mixtures of diisocyanates of the formulae (II) and (III), preferably in the ratio of 60:40 to 95:5, particularly preferably 70:30 to 90:10.

The aromatic diamines required to prepare the diisocyanates may be prepared—as known to those skilled in the art—via Friedel-Crafts alkylation of the corresponding toluenediamines with the appropriate alkene, or haloalkane. The aromatic diamines are commercial compounds which are available, for example, from Lonza AG under the trade name Lonzacure®.

Subsequently, these diamines are reacted with phosgene to give the corresponding diisocyanate.

To prepare the carbodiimides according to the invention, the diisocyanates of the formula (II) and/or (III) may be condensed, with elimination of carbon dioxide, at elevated temperatures, preferably at temperatures of 80-200° C., particularly preferably 100 to 180° C., especially preferably 120-140° C., appropriately in the presence of catalysts. Suitable methods for this purpose are described, for example, in DE-A 1130594 and DE-A 11564021.

In one embodiment of the invention, preferred catalysts for the preparation of the compounds of the formula (I) are phosphorus compounds. Phosphorus compounds used are preferably phospholene oxides, phospholidines or phospholine oxides, and the corresponding phospholene sulphides. It is also possible to use, as catalysts, tertiary amines, basic metal compounds, alkali metal or alkaline earth metal oxides, hydroxides, alkoxides or phenoxides, metal carboxylates and non-basic organometallic compounds.

The carbodiimidization can be performed either in substance or in a solvent. Solvents used are preferably alkylbenzenes, paraffin oils, polyethylene glycol dimethyl ether, ketones or lactones.

When the reaction mixture has the desired content of NCO groups, corresponding to an average degree of condensation of n=0 to 20, preferably n=1 to 10, the polycarbodiimidization is usually stopped.

In one embodiment of the present invention, the temperature of the reaction mixture is reduced for this purpose to 50-120° C., preferably 60-100° C., particularly preferably to 80-90° C. and the catalysts are distilled off under reduced pressure. In a preferred method variant of the carbodiimides according to the invention, the excess diisocyanate is subsequently distilled off at temperatures of 150-200° C., preferably 160-180° C. The free terminal isocyanate groups of the carbodiimides are then reacted with aliphatic and/or aromatic amines, alcohols and/or alkoxypolyoxyalkylene alcohols, preferably in a slight excess of —NH, —NH$_2$ and/or —OH groups, optionally in the presence of a PU catalyst known to a person skilled in the art, preferably tert, amines or organotin compounds, particularly preferably DBTL (dibutyltin dilaurate) or DOTL (dioctyltin dilaurate). The quantitative ratio of amines, alcohols and/or alkoxypolyoxyalkylene alcohols to carbodiimides is preferably 1.005-1.05:1, particularly preferably 1.01-1.03:1, based on the N=C=O groups present.

Preferred alcohols are ethanol and cyclohexanol.

In a further embodiment of the present invention, the temperature of the reaction mixture is reduced to 50-120° C., preferably 60-100° C., particularly preferably to 80-90° C. to interrupt the carbodiimidization and, optionally after addition of a solvent, preferably selected from the group of alkylbenzenes, particularly preferably toluene, the free terminal isocyanate groups of the carbodiimides are reacted with aliphatic and/or aromatic amines, alcohols and/or alkoxypolyoxyalkylene alcohols, preferably in a slight excess of —NH, —NH$_2$ and/or —OH groups, optionally in the presence of a PU catalyst known to a person skilled in the art, preferably tert. amines or organotin compounds, particularly preferably DBTL (dibutyltin dilaurate) or DOTL (dioctyltin dilaurate). The quantitative ratio of amines, alcohols and/or alkoxypolyoxyalkylene alcohols to carbodiimides is preferably 1.005-1.05:1, particularly preferably 1.01-1.03:1, based on the N=C=O groups present.

After the reaction is complete, the catalyst and optionally the solvent is distilled off under reduced pressure, preferably at temperatures of 80-200° C.

Preferred alcohols are ethanol and cyclohexanol.

The present invention also relates to a further method for preparing the carbodiimides according to the invention by a partial, preferably <50% terminal functionalization of the free NCO groups in the aromatic diisocyanates of the formula (II)

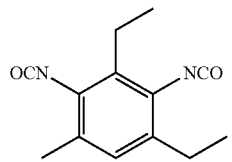

(II)

and/or of the formula (III)

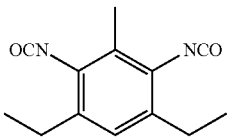

(III)

with primary or secondary amines or alcohols and/or alkoxypolyoxyalkylene alcohols and subsequent carbodiimidization with elimination of carbon dioxide at temperatures of 80° C. to 200° C. in the presence of catalysts and optionally solvent.

The carbodiimides according to the invention are preferably purified after preparation thereof. The crude products can be purified by distillation and/or by means of solvent extraction. Suitable solvents used for the purification may be, with preference, polyethylene glycol dimethyl ether, alkylbenzenes, paraffin oils, alcohols, ketones, or esters. These take the form of commercial solvents.

The present invention also relates to a composition comprising
at least one ester-based polymer, and
at least one carbodiimide of the formula (I) according to the invention.

The ester-based polymers preferably take the form of polyester polyols, ester-based thermoplastic polyurethanes, ester-based polyurethane elastomers or foams, polyethylene terephthalate (PET), polybutylene terephthalate (PBT), polytrimethylene terephthalate (PTT), copolyesters such as the modified polyester of cyclohexanediol and terephthalic acid (PCTA), thermoplastic polyester elastomers (TPE E), ethylene vinyl acetate (EVA), polylactic acid (PLA) and/or PLA derivatives, polyhydroxyalkanoates (PHA), polybutylene adipate terephthalate (PRAT), polybutylene succinate (PBS) or in blends such as preferably PA/PET or PHA/PLA blends. These take the form of commercially available polymers.

In a particularly preferred embodiment of the invention, the ester group-containing polymers are polylactic acid (PLA).

Here, the concentration of the carbodiimide of the formula (I) according to the invention in the composition according to the invention is preferably 0.1-5% by weight, preferably 0.5-3% by weight, particularly preferably 1-2% by weight.

The polyester polyols as ester-based polymers are preferably long-chain compounds that preferably have a molecular weight (in g/mol) of up to 2000, preferably between 500-2000 and more preferably between 500-1000.

The term polyester polyols in the context of the invention encompasses both long-chain diols and trials, and also compounds having more than three hydroxyl groups per molecule.

It is advantageous when the polyester polyol has an OH number of up to 200, preferably between 20 and 150 and more preferably between 50 and 115. Especially suitable are polyester polyols which are reaction products of various polyols with aromatic or aliphatic dicarboxylic acids and/or polymers of lactones.

The polyester polyols used in the context of the invention are commercially available compounds obtainable from Bayer MaterialScience AG under the Baycoll® or Desmophen® trade name.

The present invention further relates to a preferred method for preparing the carbodiimides of the formula (I) according to the invention where R=—NHCOOR$^{III}$, where R$^{III}$ is equal to C$_1$-C$_{22}$ alkyl, preferably C$_1$-C$_6$-alkyl, particularly preferably methyl, ethyl or i-propyl, C$_6$-C$_{12}$-cycloalkyl, particularly preferably C$_6$-cycloalkyl, and R$^1$, R$^2$ and R$^3$ are each independently methyl or ethyl, wherein each benzene ring has only one methyl group and n=0 to 20, preferably n=1 to 10, particularly preferably n=3 to 8, in which, after the carbodiimidization and optionally purification, the melt is pelletized, preferably on pelletizing belts. In this case, it is possible to use common pelletizing systems and likewise common granulating systems. These can be obtained, for example, from Sandvik Holding GmbH or GMF Gouda.

Especially suitable are the carbodiimides of the formula (I) according to the invention where R=—NHCOOR$^{III}$, where R$^{III}$ is cyclohexyl.

The present invention also relates to the use of the carbodiimides according to the invention as protection against hydrolytic degradation in ester-based polyols, polyethylene terephthalate (PET), polybutylene terephthalate (PBT), polytrimethylene terephthalate (PTT), copolyesters such as the modified polyester of cyclohexanediol and terephthalic acid (PCTA), thermoplastic polyester elastomers (TPE E), ethylene vinyl acetate (EVA), polylactic acid (PLA) and/or PLA derivatives, polyhydroxyalkanoates (PHA), polybutylene adipate terephthalate (PBAT), polybutylene succinate (PBS), in blends such as PA/PET or PHA/PLA blends, in triglycerides, preferably trimethylolpropane trioleate (TMP oleate), in oil formulations for the lubricants industry, in thermoplastic polyurethanes (TPU), in polyurethane elastomers, in PU adhesives, in PU casting resins, in PU foams or in PU coatings for wood, leather, artificial leather and textiles. Particular preference is given here to the use in polylactic acid (PLA).

The examples which follow serve to illustrate the invention but have no limiting effect.

WORKING EXAMPLES

Tested were:
1) CDI (A): a liquid carbodiimide having an NCN content of ca. 7.5% by weight, based on 1,3-bis(1-methyl-1-isocyanatoethyl)benzene, terminally functionalized with polyethylene glycol monomethyl ether PEG 550 MME, prepared analogously to example 2 in EP-A 0 628 541, comparative.
2) CDI (B): a liquid carbodiimide of the formula (I) having an NCN content of ca. 6% by weight, n=ca. 2, obtained by reacting a mixture based on ca. 80% by weight of 2,4-diethyltoluenediisocyanate, i.e. the diisocyanate of the formula (II), and 20% by weight of 2,6-diethyltoluenediisocyanate, i.e. the diisocyanate of the formula (III), terminally functionalized with polyethylene glycol monomethyl ether (PEG 550 MME from BASF SE), inventive.
3) CDI (C): a highly viscous carbodiimide having an NCN content of ca. 14% by weight, based on 80% by weight of 2,4-diethyltoluenediisocyanate, i.e. the diisocyanate of the formula (II), and 20% by weight of 2,6-diethyltoluenediisocyanate, i.e. the diisocyanate of the formula (III), where n>40, non-terminally functionalized (comparative).
4) CDI (D): a solid polymeric carbodiimide having an NCN content of ca. 13.5% by weight based on triisopropylphenyl diisocyanate, terminally functionalized (comparative), obtainable from Rhein Chemie Rheinau GmbH under the trade name Stabaxol® P.
5) CDI (E): a monomeric solid carbodiimide having an NCN content of ca. 10.8% by weight based on 2,6-diisopropylphenyl isocyanate (comparative), obtainable from Rhein Chemie Rheinau GmbH under the trade name Stabaxol® I.
6) CDI (F): a solid carbodiimide having an NCN content of ca. 12.5% by weight, based on ca. 80% by weight of 2,4-diethyltoluenediisocyanate, i.e. the diisocyanate of the formula (II), and 20% by weight of 2,6-diethyltoluenediisocyanate, i.e. the diisocyanate of the formula (III), terminally functionalized with ethanol where n=ca. 6, inventive.
7) CDI (G): a solid carbodiimide having are NCN content of ca. 10.2% by weight, based on ca. 80% by weight of 2,4-diethyltoluenediisocyanate, i.e. the diisocyanate of the formula (II), and 20% by weight of 2,6-diethyltoluenediisocyanate, i.e. the diisocyanate of the formula (III), terminally functionalized with cyclohexanol where n=ca. 5, inventive.

Ester-Based Polymers:
8) Polyester polyol based on adipic acid (Desmophen® 2001 KS from Bayer MaterialScience AG).
9) Polyethylene terephthalate (PET) obtainable from Novapet.
10) Polylactic acid (PLA, injection moulding quality) obtainable from NatureWorks LLC.

Preparation of the Inventive Carbodiimide CDI (B)

A baked-out and nitrogen-filled 250 ml four-neck flask was charged under a nitrogen stream with 92 g of a mixture consisting of ca. 20% by weight of 2,6-diethyltoluenediisocyanate and ca. 80% by weight of 2,4-diethyltoluenediisocyanate. After addition of 50 mg of 1-methylphospholene oxide the mixture was heated to 130° C. Thereafter, carbodiimidization was continued at 130° C. until an NCO content of ca. 12% by weight had been attained. The catalyst was then removed completely by distillation under vacuum at a temperature of ca. 120° C. and the excess diisocyanate was distilled off under vacuum at a temperature of ca. 180° C. Finally, the reaction mixture was cooled to ca. 90-100° C. and the terminal NCO groups were reacted with PEG 500 MME. The resulting product was a light, yellow liquid having an NCN content of ca. 6% by weight and a polydispersity (Mw/Mn) of ca. 1.5.

Preparation of the Carbodiimide CDI (C)

A baked-out and nitrogen-filled 250 ml four-neck flask was charged under a nitrogen stream with 150 g of a mixture consisting of ca. 20% by weight of 2,6-diethyltoluenediisocyanate and ca. 80% by weight of 2,4-diethyltoluenediisocyanate. After addition of 50 mg of 1-methylphospholene oxide the mixture was heated to 180° C. Thereafter, carbodiimidization was continued at 180° C. until an NCO content of <1% by weight had been attained. The resulting product was a dark, sticky, solidified melt having an NCN content of ca. 14% by weight.

Preparation of the Inventive Carbodiimide CDI (F) and CDI (G):

A baked-out and nitrogen-filled 250 ml four-neck flask was charged under a nitrogen stream with 92 g of a mixture consisting of ca. 20% by weight of 2,6-diethyltoluenediisocyanate and ca. 80% by weight of 2,4-diethyltoluenediisocyanate. After addition of 50 mg of 1-methylphospholene oxide the mixture was heated to 130° C. Thereafter, carbodiimidization was continued at 130° C. until an NCO content of ca. 7-9% by weight had been attained. The catalyst was then removed completely by distillation under vacuum at a temperature of ca. 120° C. and the excess diisocyanate was distilled off under vacuum at a temperature of ca. 180° C. Finally, the reaction mixture was cooled to ca. 70-80° C. and the terminal NCO groups, after addition of toluene as solvent, were reacted with ethanol (CDI F) or cyclohexanol (CDI G). After removal of the solvent by distillation, solids were obtained having an NCN content of ca. 12.5% by weight (CDI F) or 10.2% by weight (CDI G) and a polydispersity (Mw/Mn) of ca. 1.8.

Thermal Stability

To investigate the thermal stability at 80° C., 1% by weight of the abovementioned carbodiimides was stirred into polyester polyol having an initial acid number of ca. 0.9 mg KOH/g and the mixture was stirred further at this temperature for 3 h. The gas phase was investigated by GC-MS on the cleavage substances (isocyanates). The results are shown in Table 1:

| Carbodiimide | Detection of cleavage substances (isocyanates) |
| --- | --- |
| CDI (A) (C) | Negative |
| CDI (B) (inv.) | Negative |

C = comparative example,
inv. = inventive

It is evident from Table 1 that the inventive carbodiimide CDI (B) has excellent thermal stability which is comparable to CDI (A).

Acid Number Decrease in Polyester Polyol

As is known, the effect of a hydrolysis stabilizer based on sterically hindered carbodiimides in liquid polyester polyols can be tested by means of the decrease in acid number.

The decrease in acid number in the composition according to the invention was tested using the inventive CDI (B) compared to the CDI (A) known from the prior art in a polyester polyol based on adipic acid (Desmophen® 2001 KS from Bayer MaterialScience AG).

For this purpose, at 80° C., 1% by weight of the abovementioned carbodiimides was stirred into polyester polyol having an initial acid number of ca. 0.9 mg KOH/g and the acid number was measured at regular intervals.

The results are shown in Table 2:

| Carbodiimide in Desmophen® 2001 KS | Acid number [mg KOH/g] after 0 min | Acid number [mg KOH/g] after 30 min | Acid number [mg KOH/g] after 60 min | Acid number [mg KOH/g] after 120 min | Acid number [mg KOH/g] after 240 min | Acid number [mg KOH/g] after 480 min |
|---|---|---|---|---|---|---|
| CDI (B) (inv.) | 0.86 | 0.63 | 0.52 | 0.38 | 0.21 | 0.12 |
| CDI (A) (C) | 0.87 | 0.69 | 0.55 | 0.42 | 0.35 | 0.28 |

C = comparative example,
inv. = inventive

The results show that the residual acid of the polyester polyol with the inventive carbodiimide is surprisingly degraded much more quickly, despite the lower NCN content, than in the composition comprising the CDI (A) known from the prior art.

Protection Against Hydrolysis in Polyethylene Terephthalate (PET)

To evaluate the hydrolysis-stabilizing effect in PET, 1.5% by weight of the carbodiimides under investigation were each dispersed into PET by means of a laboratory twin screw extruder ZSK 25 from Werner & Pfleiderer prior to the measurement described below. F3 standard test specimens used for measuring the tensile strength were than prepared from the pellets obtained on an injection moulding machine of the type Arburg Allrounder 320 S 150-500.

For the hydrolysis test, these F3 standard test specimens were stored in water vapour at a temperature of 110° C. and the tensile strength thereof measured in MPa.

The results are listed in Table 3:

| Tensile strength (MPa) | Ex. 1 (comp.) (PET) | Ex. 2 (comp.) (PET, 1 x extruded) | Ex. 3 (comp.) (PET/ CDI A) | Ex. 4 (comp.) (PET/ CDI D) | Ex. 5 (inv.) (PET/ CDI F) | Ex. 6 (inv.) (PET/ CDI G) |
|---|---|---|---|---|---|---|
| Day 0 | 84 | 62 | 82 | 88 | 80 | 89 |
| 1 day | 73 | 41 | 62 | 76 | 77 | 77 |
| 2 days | 72 | 21 | — | — | — | — |
| 3 days | 50 | 0 | 2 | 76 | 72 | 71 |
| 4 days | 25 | | 0 | 70 | 68 | 68 |
| 5 days | 8 | | | 37 | 37 | 46 | comp. = comparative example,
inv. = inventive

Protection Against Hydrolysis in Polylactic Acid (PLA)

To evaluate the hydrolysis-stabilizing effect in PLA, 1.0 or 1.5% by weight of the carbodiimides under investigation were each dispersed into PLA by means of a laboratory twin screw extruder ZSK 25 from Werner & Pfleiderer prior to the measurement described below. F3 standard test specimens used for measuring the tensile strength were then prepared from the pellets obtained on an injection moulding machine of the type Arburg Allrounder 320 S 150-500.

For the hydrolysis test, these F3 standard test specimens were stored in water at a temperature of 65° C. and the tensile strength thereof measured.

The results are listed in Table 4:

| Tensile strength (MPA) | Ex. 7 (comp.) (PLA) | Ex. 8 (comp.) (PLA, CDI E) 1.0%/1.5% | Ex. 9 (comp.) (PLA, CDI D) 1.0%/1.5% | Ex. 10 (inv.) (PET, CDI F) 1.0%/1.5% |
|---|---|---|---|---|
| 0 days | 76 | 75/73 | 77/74 | 77/75 |
| 1 day | 63 | 67/— | — | — |
| 2 days | 47 | 69/— | — | — |
| 3 days | 25 | 58/— | 73/73 | 74/75 |
| 4 days | 7 | 32/— | 61/71 | — |
| 5 days | 0 | — | — | — |
| 7 days | | 0/46 | 8/43 | 50/74 |
| 8 days | | —/37 | 0/35 | 41/— |
| 9 days | | —/19 | —/21 | 23/74 |
| 10 days | | —/10 | —/15 | 8/74 |
| 15 days | | —/0 | —/0 | 0/63 |
| 18 days | | | | —/53 | comp. = comparative example,
inv. = inventive
% = data in % by weight

The data in Table 4 correspond to the values of 1.0%/1.5% of the relevant CDIs.

The results from Tables 3 and 4 show that the carbodiimides according to the invention show excellent protection against hydrolysis in PET and PLA compared to the prior art. Moreover, these have the advantage that these are based on more favourable raw materials and are considerably less expensive to manufacture.

Experiments on the Ability to Pelletize and Meterability of the Solid Carbodiimides To elucidate the finishability, handling and meterability of the various solid carbodiimides, these were compared with respect to appearance, ability to pelletize and softening point. The softening points were determined by means of a Kofller bank.

The results are listed in Table 5:

| Carbodiimide | Appearance (at RT) | Ability to pelletize | Meterability (T to 40° C.). | Softening point (° C.) |
|---|---|---|---|---|
| CDI (C), comp. | hard, sticky mass | not possible | not possible | <20 |
| CDI (D), comp. | solid, brittle | very good | satisfactory | ca. 50 |
| CDI (E), comp. | solid, waxy | not possible | adequate | <40 |
| CDI (F) (inv.) | solid, brittle | very good | good | >50 |
| CDI (G) (inv.) | solid, brittle | very good | very good | >60 | comp. = comparative example,
inv. = inventive

The results from Table 5 clearly show that the carbodiimides according to the invention based on diethyltoluenediisocyanate end-capped with ethanol or cyclohexanol, despite the lower degree of polymerization, have excellent capacity for pelletization and a high softening point compared to the polymeric carbodiimide based on diethyltoluenediisocyanate (non-terminally functionalized) and therefore entail advantages in the finishing and metered addition of the solid in the stabilization of the ester-based polymers.

What is claimed is:

1. Carbodiimides having terminal urea and/or urethane groups, the carbodiimides being of the formula (I)

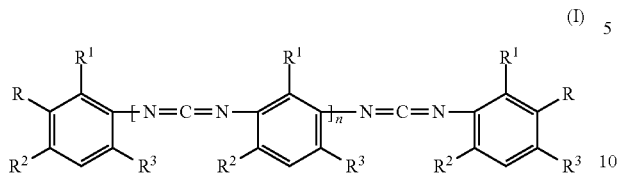

in which each R may be the same or different and is selected from the group of —NHCONHR$^I$, —NHCONR$^I$R$^{II}$ and —NHCOOR$^{III}$ residues, where R$^I$ and R$^{II}$ are the same or different and are a $C_1$-$C_{22}$-alkyl, $C_6$-$C_{12}$-cycloalkyl, $C_6$-$C_{18}$-aryl or $C_6$-$C_{18}$-aralkyl residue, and R$^{III}$ corresponds to $C_1$-$C_{22}$-alkyl, $C_6$-$C_{12}$-cycloalkyl, $C_6$-$C_{18}$-aryl or $C_6$-$C_{18}$-aralkyl, or an unsaturated alkyl residue having 2-22 carbon atoms, or an alkoxypolyoxyalkylene residue, $R^1$, $R^2$ and $R^3$ are each independently methyl or ethyl, wherein each benzene ring has only one methyl group, and n=0 to 20.

2. The carbodiimides according to claim 1, wherein each R is an —NHCOOR$^{III}$ residue, where R$^{III}$ is an alkoxypolyoxyalkylene or an unsaturated alkyl residue having 18 carbon atoms.

3. The carbodiimides according to claim 1, wherein each R is an —NHCOOR$^{III}$ residue, where R$^{III}$ is a $C_1$-$C_{22}$-alkyl, or $C_6$-$C_{12}$-cycloalkyl.

4. The carbodiimides according to claim 1, wherein each R is an —NHCOOR$^{III}$ residue, where R$^{III}$ is a polyethylene glycol monomethyl ether with molar masses of 200-600 g/mol.

5. The carbodiimides according to claim 2, wherein the carbodiimide has an NCN content of 2-14% by weight.

6. The carbodiimides according to claim 3, wherein the carbodiimide has an NCN content of 2-14% by weight.

7. The carbodiimides according to claim 1, wherein the carbodiimides have:
average molar masses (Mw) of 1000-5000 g/mol, and a polydispersity D=Mw/Mn of 1.2-2.

8. The carbodiimides according to claim 1, wherein:
each R is an —NHCOOR$^{III}$ residue;
n=1 to 10; and
the carbodiimides have an NCN content of 2-14% by weight, average molar masses (Mw) of 2000-3000 g/mol, and a polydispersity D=Mw/Mn of 1.4-1.8.

9. A method for preparing the carbodiimides according to claim 1, the method comprising:
carbodiimidizing diisocyanates of at least one of the formula (II)

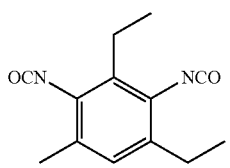

and of the formula (III)

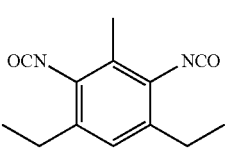

with elimination of carbon dioxide at temperatures of 80° C. to 200° C. in the presence of catalysts and optionally solvent, and subsequently, terminally functionalizing the free NCO functionalities with primary or secondary amines or alcohols.

10. A method for preparing the carbodiimides according to claim 1, the method comprising:
at least partially, terminally functionalizing free NCO groups in aromatic diisocyanates of at least one of the formula (II)

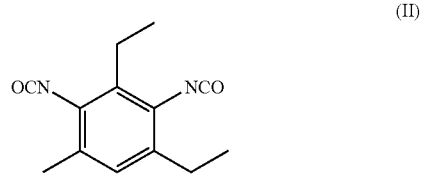

and of the formula (III)

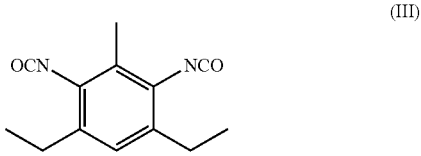

with primary or secondary amines or alcohols, and/or alkoxypolyoxyalkylene alcohols to produce an intermediary, and subsequently, carbodiimidizing the intermediary with elimination of carbon dioxide at temperatures of 80° C. to 200° C. in the presence of catalysts and optionally solvent.

11. The method according to claim 9, wherein the carbodiimidization is carried out at temperatures of 80-200° C., and subsequently, optionally after distilling off the catalyst at temperatures of 50-120° C. and the unreacted diisocyanate at temperatures of 160-180° C., reacting the remaining NCO groups of the carbodiimide with aliphatic and/or aromatic amines, alcohols and/or alkoxypolyoxyalkylene alcohols, at temperatures of 80-140° C., optionally in the presence of a PU catalyst.

12. The method according to claim 9, wherein the carbodiimidization is carried out at temperatures of 80-200° C., and subsequently the temperature of the reaction mixture is reduced to 50-120° C., to interrupt the carbodiimidization and, after optional addition of a solvent, reacting the free terminal isocyanate groups of the carbodiimides with aliphatic and/or aromatic amines, alcohols and/or alkoxypolyoxyalkylene alcohols.

13. The method for preparing carbodiimides according to claim 9, wherein the method comprises carbodiimidizing a mixture of diisocyanates of the formula (II) and (III) in a ratio of 70:30 to 90:10.

14. The method for preparing the carbodiimides according to claim 9, wherein:
each R is an —NHCOOR$^{III}$ residue, where R$^{III}$ is a $C_1$-$C_{22}$-alkyl, or $C_6$-$C_{12}$-cycloalkyl; and
the method further comprises pelletizing the carbodiimides after the carbodiimidization.

15. The method according to claim 14, wherein $R^{III}$=cyclohexyl.

16. A composition comprising:
at least one ester-based polymer; and
at one carbodiimide according to claim 1.

17. The composition according to claim 16, wherein the composition comprises 0.1-5% by weight of the carbodiimide.

18. A method for preparing the compositions according to claim 16, wherein:
$R^{III}$=cyclohexyl, and the ester-based polymers are selected from the group consisting of polyethylene terephthalate (PET), polybutylene terephthalate (PBT), polytrimethylene terephthalate (PTT), thermoplastic polyurethanes (TPU), copolyesters, thermoplastic polyester elastomers (TPE E), ethylene vinyl acetate (EVA), polylactic acid (PLA), polybutylene adipate terephthalate (PRAT), polybutylene succinates (PBS), PLA derivatives and polyhydroxyalkanoates (PHA), and
the method comprises adding the carbodiimides by means of a solids metering unit to the ester-based polymers.

19. A method for protecting against hydrolytic degradation in polymers, the method comprising incorporating the carbodiimides according to claim 1 in ester-based polyols, in polyethylene terephthalate (PET), in polybutylene terephthalate (PBT), in polytrimethylene terephthalate (PTT), in copolyesters, in thermoplastic polyester elastomers (TPE E), in ethylene vinyl acetate (EVA), in polylactic acid (PLA) and/or in PLA derivatives, in polybutylene adipate terephthalates (PBAT), in polybutylene succinates (PBS), in polyhydroxyalkanoates (PHA), in blends, in triglycerides, in oil formulations for the lubricants industry, in thermoplastic polyurethanes (TPU), in polyurethane elastomers, in PU adhesives, in PU casting resins, in PU foams, or in PU coatings for wood, leather, artificial leather and textiles.

20. A method for protecting against hydrolytic degradation in polylactic acid, the method comprising incorporating the carbodiimides according to claim 1 in polylactic acid (PLA).

21. The composition according to claim 16, wherein:
the at least one ester-based polymer is selected from the group consisting of polyester polyols, ester-based thermoplastic polyurethanes, polyurethane elastomers, PU adhesives, PU casting resins, polyethylene terephthalates (PET), polybutylene terephthalates (PBT), polytrimethylene terephthalates copolyesters, thermoplastic polyester elastomers (TPE E), ethylene vinyl acetates (EVA), polylactic acids (PLA), polybutylene adipate terephthalates (PBAT), polybutylene succinates (PBS), PLA derivatives and polyhydroxyalkanoates (PHA); and
the composition comprises 1-2% by weight of the carbodiimides.

* * * * *